ROSE PLANT
Filed Oct. 20, 1975
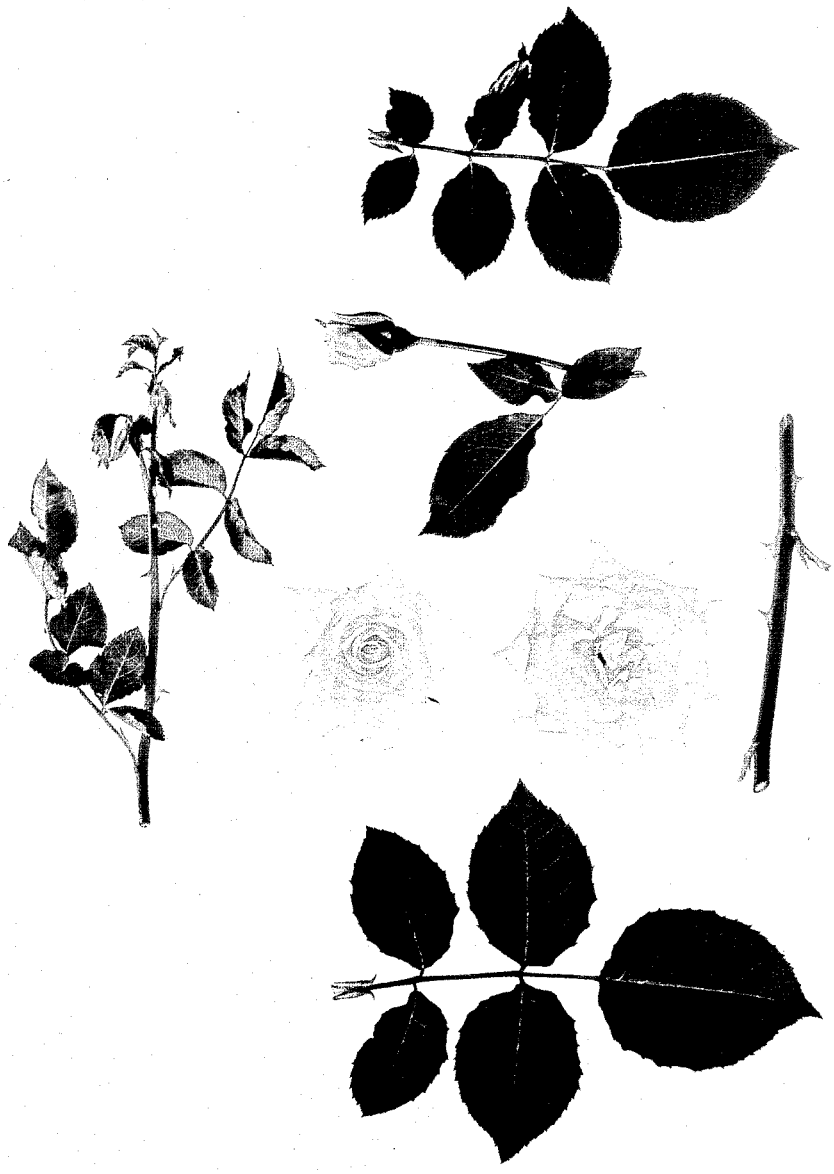

United States Patent

Plant Pat. 3,975

Patented Nov. 16, 1976

3,975

ROSE PLANT

Robert G. Jelly, Richmond, Ind., assignor to E. G. Hill Co., Inc., Richmond, Ind.

Filed Oct. 20, 1975, Ser. No. 623,061

Int. Cl.[2] A01H 5/00

U.S. Cl. Plt.—24 1 Claim

ABSTRACT OF THE DISCLOSURE

A new variety of yellow rose plant intended for greenhouse culture and the production of cut flowers, this new variety being distinguished by its erect and uniform habit of growth, its superior pointed bud, its distinctive flower color, its free and continuous production of medium large flowers, and its lustrous foliage

BACKGROUND OF THE INVENTION

My new variety of rose plant originated as a seedling of Golden Garnette (P.P. 1,898) resulting from a cross with an undisseminated seedling out of Golden Rapture (P.P. 1,413) identified in my record as No. 1–61YS, this cross having been made in spring 1968 and the first flower being brought to maturity in the spring of 1969.

This crossing was made by me in the course of breeding efforts being carried on by me at Richmond, Ind., with the object of obtaining a plant having the bloom color and foliage of the pollen parent and the uniformity of growth and the vigor of the seed parent, and the apparent retention of these features in the new plant led to its being reproduced by me, by grafting, at Richmond, Ind. Succeeding propagations of this new variety carried on by grafting at Richmond, Ind., and by budding at Livermore, Calif., have demonstrated that the distinguishing and advantageous characteristics of the original plant are firmly fixed and hold true from generation to generation.

DESCRIPTION OF THE DRAWING

This new variety of rose plant is illustrated by the accompanying full color photographic drawing which shows face views of a newly opened flower and a mature or fully opened flower, a typical bud shortly after the calyx breaks, the upper and under sides of young and mature leaves, a specimen of young stem with foliage and a specimen of mature wood; all colors being shown as nearly true as it is reasonably possible to obtain by conventional commercial photographic procedures.

DESCRIPTION OF THE NEW PLANT

The following is a detailed description of my new variety of rose plant with the color designations being stated as determined by reference to the Royal Horticultural Society Colour Chart (RHS) and the Horticultural Colour Chart by Robert S. Wilson published by the Royal Horticultural Society at London, England (HCC).

The plant

Origin: Seedling (identified as 57–70YS).

Parentage:

*Seed parent.*—Golden Garnette (P.P. 1,898).

*Pollen parent.*—1–61YS, an undisseminated seedling out of Golden Rapture (P.P. 1,413).

Classification:

*Botanic.*—Rosa hybrid.

*Commerical.*—Floribunda, Greenhouse rose, for cut flowers.

Form: Bush.

Growth: Moderately free and vigorous.

Habit: Upright and much branched.

Canes: Medium diameter.

Main stems: Moderately strong and of medium length.

*Color.*—Green 137C (RHS).

*Thorns.*—Several, medium length, some straight and some angled slightly downward, all with a long broad base. Color: Greyed Orange 165A (RHS) at base fading to a shade between 165B and 165C at the tip.

*Prickles and Hairs.*—None.

Branches: Color—Green 137C (RHS).

*Thorns.*—Several, of medium length, slightly angled downward from a long and broad base.

*Color.*—Yellow Green 146D (RHS) with a slight veination of Greyed Purple 185C at the base and fading slightly lighter than 146D at the tip.

*Prickles and Hairs.*—None.

Foliage: Leaves are compound and odd pinnate. Size—Normally medium small.

*Leaflets.*—3 to 7 in number. Shape: Oval, with cuspidate apex, obtuse base and serrate margin. Color: Young Leaflets: Upper surface—Yellow Green 144A (RHS) along main vein and toward the tip, shaded with and bordered with Garnet Brown 00918 (HCC). Under surface—Yellow Green 144C (RHS) down mid-vein and overcast with veins of Greyed Purple 183B to 189A (RHS) at the margin. Mature leaflets: Upper surface—More glossy than Ivy Green 0001060/1 (HCC). Under surface—A shade slightly darker than Leek Green 000858 (HCC). Texture: Moderately thick and leathery. Aspect: Glossy.

*Rachis.*—Medium in length. Grooved and prickly on upper side and thorny on under side.

*Stipules.*—Medium in length and width, with points which are medium long and which turn out at an angle of less than 45° and recurve toward the stem.

The bud

Size: Before the calyx breaks, the bud size is medium small. The form is short pointed with a conspicuous neck having slender bristle-like foliaceous parts extending beyond the tip of the bud for a distance equal to about one-half or more of the bud length. As the first petal opens, the bud size is still small and the bud form is ovid.

Color: Before the calyx breaks, the color in the center of the sepals is Yellow Green 144C (RHS) to Yellow Green 144A at the margins with Greyed Purple 184B (RHS) at the tips of the foliaceous parts. As the calyx breaks, the outside petal color is Yellow 7C (RHS). As the first petals open, the color of the outside of the petals is slightly lighter than Yellow Orange 14B (RHS) and the inside is Yellow Orange 15A.

Opening: In greenhouse, the bud does open up well. In hot dry weather, there is a slight decrease of bud size and a slightly lighter overall color intensity.

Peduncle: Medium in length, erect and small in diameter.

*Bark.*—Entirely smooth. Color: Yellow Green 144B (RHS).

*Thorns.*—None.

*Prickles.*—Numerous. Color: Greyed Red 182B (RHS) at the base, fading to translucent at the tip.

*Hairs.*—None.

The flower

Blooming habit: Free in quantity and continuity is continuous in greenhouse.

Size: When fully opened—large, 3½ to 4 inches in diameter.

Form: High centered at first, becoming open to high centered, petals being loosely rolled outward at first and becoming very rolled at maturity.

Borne: Several to a stem.

Petalage: Double—from 28 to 34 petals regularly arranged.

*Shape.*—Outside petals: Ovate mucronate apex and having 1 or 2 notches. Intermediate and inside petals: Obovate with apex of some being mucronate with 1 or 2 notches.

*Texture.*—Moderately thick and leathery.

*Aspect.*—Satiny on inside, shiny on outside.

Color: The colors described may be modified by being shaded with other colors.

The following is the color description of a newly open flower as observed in greenhouse in the month of February 1975 at Richmond, Ind.

Outside petals:

*Outer surface.*—Lemon Yellow 4/3 (HCC) at the base, shading to slightly lighter than Dresden Yellow 64/2 (HCC) at the margins and apex.

*Inside surface.*—Lemon Yellow 4/1 (HCC) at the base, shaded to Dresden Yellow 64/3 (HCC) at the margins and apex.

Intermediate petals:

*Outer surface.*—Lemon Yellow 4/1 (HCC) at the base to a shade slightly lighter than Yellow 10A (RHS) at the margin.

*Inside surface.*—From a shade between Lemon Yellow 4 and 4/1 (HCC) at the base to Yellow 10A (RHS) at the margins and apex.

Inner petals:

*Outer surface.*—Lemon Yellow 4/1 (HCC) at the base to a shade slightly darker than Yellow 13B (RHS) but not as dark as Yellow 13A.

*Inside surface.*—Lemon Yellow 4 (HCC) at the base to Aureolin 3 (HCC) at the margins and the apex.

The following is a color description of a flower opened three days in greenhouse at Richmond, Ind., in the month of February 1975.

Outside petals:

*Outer surface.*—Slightly darker than Yellow 7B (RHS) at base, fading to slightly lighter than Yellow 4C and bleaching to Yellow 4D at the margin.

*Inside surface.*—Yellow 7A (RHS) at the base fading rapidly to 601/3 (HCC), the main color of the inside surface.

Intermediate petals:

*Outer surface.*—Yellow 9B (RHS) at the base fading through shades slightly lighter than 9B to Yellow 6C at the apex.

*Inside surface.*—Fading from a shade slightly darker than Empire Yellow 603 (HCC) at the base, through Mimosa Yellow 602/1 to Dresden Yellow 64/3 (HCC) at the apex.

Inside petals:

*Outside surface.*—Fading from a shade between 603 and 603/1 (HCC) at the base to slightly lighter than Yellow 7D (RHS) at the apex.

*Inside surface.*—Fading rapidly from 603 (HCC) at the base to 602/2 (HCC) at the apex.

General color effect:

*Newly opened flower.*—From Lemon Yellow 4 (HCC) at the center bleaching to Dresden Yellow 64 (HCC) at the margin of outside petals in warm weather.

*Three Days opened flower.*—From Mimosa Yellow 602 (HCC) at the center to shades of Dresden Yellow 64/3 (HCC) and Primrose Yellow 601/3 (HCC) at the border petals.

Sepals: Permanent, of medium length.

*Color.*—Inside of sepals—Pod Green 061/2 (HCC) at the base and along the veins shading to Yellow Green 147C (RHS) toward the margin. Outside of sepals—Yellow Green 145B (RHS) at the base and along the vein to Yellow Green 144A (RHS) which is the main color to the margin.

Fragrance: In greenhouse—penetrating spicy.

Persistence: The petals hang on and dry.

Effect of weather: In hot, dry weather, the colors are a shade lighter in intensity and the bud size is slightly smaller.

Lasting quality: Seven days at living room temperature. (Observed in July 1975.)

Reproductive organs

Stamens: Many in number, regularly arranged and mixed with petaloids.

*Filaments.*—Some long, some of medium length, most with anthers. Color: The longer filaments are a shade between Yellow 9B and 9C (RHS); the shorter filaments are Greyed Orange 168B (RHS) at the base shading to 9C (RHS) at the top.

*Anthers.*—Medium to large in size; most open all at once. Color: Shades between Yellow 10C (RHS) and Yellow 9D (RHS) in the center, bordered by Greyed Orange 171C (RHS).

Pollen: Moderate. Color: Yellow Orange 20A (RHS).

Pitsils: Few in number.

*Styles:* Uneven, short to medium in length, thin and bunched. Color: A blend of Naples Yellow 403/2 and 403/1 (HCC) at the base to shades of Cardinal Red 822/2 and 822/3 (HCC) for the main portion.

*Stigmas.*—Color—Orange Buff 508 (HCC).

Ovaries: All encased, in calyx.

Hips: Short in length, flat at top and globular, with conspicuous neck, gourd shaped with very smooth thick walls.

Seeds: Many of medium size.

My new variety of rose plant is an improvement over its seed parent, Golden Garnette (P.P. 1,898), in that it has a much superior bud form, flower color, and a harder and more lustrous foliage while retaining the vigor and uniformity of growth of the seed parent and yet maintaining the bloom color and foliage character of the pollen parent 1–16YS (unpatented). This new yellow floribunda has an erect uniform growth habit with a superior pointed bud and an excellent yellow color.

I claim:

1. A new and distinct variety of rose plant substantially as herein shown and described, characterized by its superior bud form, flower color, and its harder and more lustrous foliage compared to its seed parent, and by its free and continuous production of large flowers on moderately strong stems of medium length.

No references cited.

ROBERT E. BAGWILL, Primary Examiner